(12) United States Patent
Kim et al.

(10) Patent No.: US 11,504,386 B2
(45) Date of Patent: Nov. 22, 2022

(54) PREPARATION METHOD FOR VARIOUS NOVEL FUCOSYL OLIGOSACCHARIDES AND USE THEREOF

(71) Applicant: Korea University Research and Business Foundation, Seoul (KR)

(72) Inventors: Kyoung Heon Kim, Seoul (KR); Yong-Su Jin, Champaign, IL (US); Eun-Ju Yun, Seoul (KR); Sora Yu, Gyeonggi-do (KR); Jaewon Lee, Urbana, IL (US)

(73) Assignee: Korea University Research and Business Foundation, Seoul (KR)

( * ) Notice: Subject to any disclaimer, the term of this patent is extended or adjusted under 35 U.S.C. 154(b) by 23 days.

(21) Appl. No.: 16/765,359

(22) PCT Filed: Nov. 15, 2018

(86) PCT No.: PCT/KR2018/014000
§ 371 (c)(1),
(2) Date: May 19, 2020

(87) PCT Pub. No.: WO2019/098706
PCT Pub. Date: May 23, 2019

(65) Prior Publication Data
US 2020/0338101 A1  Oct. 29, 2020

(30) Foreign Application Priority Data
Nov. 20, 2017 (KR) ................ 10-2017-0154840

(51) Int. Cl.
*A61K 31/7004* (2006.01)
*A23L 33/125* (2016.01)
*A61K 8/60* (2006.01)
*A61K 31/7016* (2006.01)
*A61K 31/729* (2006.01)
*C12P 19/04* (2006.01)
*C12P 19/18* (2006.01)

(52) U.S. Cl.
CPC ........ *A61K 31/7004* (2013.01); *A23L 33/125* (2016.08); *A61K 8/602* (2013.01); *A61K 31/7016* (2013.01); *A61K 31/729* (2013.01); *C12P 19/04* (2013.01); *C12P 19/18* (2013.01)

(58) Field of Classification Search
CPC ............... A61K 31/7004; A61K 8/602; A61K 31/7016; A61K 31/729; A23L 33/125; C12P 19/04; C12P 19/18
USPC .......................................................... 514/25
See application file for complete search history.

(56) References Cited

U.S. PATENT DOCUMENTS

| | | | | |
|---|---|---|---|---|
| 2004/0048331 | A1* | 3/2004 | Taylor | C12N 9/1051 435/68.1 |
| 2004/0058418 | A1* | 3/2004 | Endo | C12N 9/1051 536/123 |
| 2012/0294840 | A1 | 11/2012 | Newburg et al. | |
| 2015/0231159 | A1 | 8/2015 | Hernandez et al. | |
| 2015/0290261 | A1 | 10/2015 | Chichlowski et al. | |

FOREIGN PATENT DOCUMENTS

| | | | |
|---|---|---|---|
| DE | 2479263 | * | 7/2012 |
| KR | 10-2014-0032983 A | | 3/2014 |
| KR | 10-1544184 B1 | | 8/2015 |
| WO | 2012/097950 A1 | | 7/2012 |

OTHER PUBLICATIONS

Sakai et al. Synthesis of ß-D-Fucosylglucose by ß-D-Glucosidase I of Bifidobacterium breve clb and Assimilation by Bifidobacteria. Agric. Biol. Chem., 53 (2), 313~318, 1989. (Year: 1989).*
Sequence search result in the docket, 20211117_154508_us-16-765-359-2, Run on: Nov. 17, 2021. (Year: 2021).*
International Search Report for PCT/KR2018/014000 dated May 15, 2019 [PCT/ISA/210].
Written Opinion for PCT/KR2018/014000 dated May 15, 2019 [PCT/ISA/237].

* cited by examiner

*Primary Examiner* — Yih-Horng Shiao
(74) *Attorney, Agent, or Firm* — Sughrue Mion, PLLC

(57) ABSTRACT

The present invention relates to a preparation method for various novel fucosyl oligosaccharides and a use thereof. More specifically, the present invention allows a preparation of various novel fucosyl oligosaccharides through an enzymatic reaction with α-1,2-fucosyltransferase using a GDP-L-fucose donor and various glucose acceptors and an establishment of probiotic characteristics thereof, and thus has an effect of providing uses as materials for medicines, food, cosmetic products, and the like.

5 Claims, 9 Drawing Sheets

Specification includes a Sequence Listing.

SEQUENCE LISTING

```
<160> NUMBER OF SEQ ID NOS: 3

<210> SEQ ID NO 1
<211> LENGTH: 287
<212> TYPE: PRT
<213> ORGANISM: Bacteroides fragilis

<400> SEQUENCE: 1

Met Leu Tyr Val Ile Leu Arg Gly Arg Leu Gly Asn Asn Leu Phe Gln
1               5                   10                  15

Ile Ala Thr Ala Ala Ser Leu Thr Gln Asn Phe Ile Phe Cys Thr Val
            20                  25                  30

Asn Lys Asp Gln Glu Arg Gln Val Leu Leu Tyr Lys Asp Ser Phe Phe
        35                  40                  45

Lys Asn Ile Lys Val Met Lys Gly Val Pro Asp Gly Ile Pro Tyr Tyr
    50                  55                  60

Lys Glu Pro Phe His Glu Phe Ser Arg Ile Pro Tyr Glu Glu Gly Lys
65                  70                  75                  80

Asp Leu Ile Ile Asp Gly Tyr Phe Gln Ser Glu Lys Tyr Phe Lys Arg
                85                  90                  95

Ser Val Val Leu Asp Leu Tyr Arg Ile Thr Asp Glu Leu Arg Lys Lys
            100                 105                 110

Ile Trp Asn Ile Cys Gly Asn Ile Leu Glu Lys Gly Glu Thr Val Ser
        115                 120                 125

Ile His Val Arg Arg Gly Asp Tyr Leu Lys Leu Pro His Ala Leu Pro
    130                 135                 140

Phe Cys Gly Lys Ser Tyr Tyr Lys Asn Ala Ile Gln Tyr Ile Gly Glu
145                 150                 155                 160

Asp Lys Ile Phe Ile Ile Cys Ser Asp Asp Ile Asp Trp Cys Lys Lys
                165                 170                 175

Asn Phe Ile Gly Lys Arg Tyr Tyr Phe Ile Glu Asn Thr Thr Pro Leu
            180                 185                 190

Leu Asp Leu Tyr Ile Gln Ser Leu Cys Thr His Asn Ile Ile Ser Asn
        195                 200                 205

Ser Ser Phe Ser Trp Trp Gly Ala Trp Leu Asn Glu Asn Ser Asn Lys
    210                 215                 220

Ile Val Ile Ala Pro Gln Met Trp Phe Gly Ile Ser Val Lys Leu Gly
225                 230                 235                 240

Val Ser Asp Leu Leu Pro Val Ser Trp Val Arg Leu Pro Asn Asn Tyr
                245                 250                 255
```

```
Thr Leu Gly Arg Tyr Cys Phe Ala Leu Tyr Lys Val Val Glu Asp Tyr
            260                 265                 270

Leu Leu Asn Ile Leu Arg Leu Ile Trp Lys Arg Lys Lys Asn Met
    275                 280                 285

<210> SEQ ID NO 2
<211> LENGTH: 297
<212> TYPE: PRT
<213> ORGANISM: E. coli O126

<400> SEQUENCE: 2

Met Ser Ile Ile Arg Leu Gln Gly Gly Leu Gly Asn Gln Leu Phe Gln
1               5                   10                  15

Phe Ser Phe Gly Tyr Ala Leu Ser Lys Ile Asn Gly Thr Pro Leu Tyr
            20                  25                  30

Phe Asp Ile Ser His Tyr Ala Glu Asn Asp Asp His Gly Gly Tyr Arg
        35                  40                  45

Leu Asn Asn Leu Gln Ile Pro Glu Glu Tyr Leu Gln Tyr Tyr Thr Pro
    50                  55                  60

Lys Ile Asn Asn Ile Tyr Lys Leu Leu Val Arg Gly Ser Arg Leu Tyr
65                  70                  75                  80

Pro Asp Ile Phe Leu Phe Leu Gly Phe Cys Asn Glu Phe His Ala Tyr
                85                  90                  95

Gly Tyr Asp Phe Glu Tyr Ile Ala Gln Lys Trp Lys Ser Lys Lys Tyr
            100                 105                 110

Ile Gly Tyr Trp Gln Ser Glu His Phe Phe His Lys His Ile Leu Asp
        115                 120                 125

Leu Lys Glu Phe Phe Ile Pro Lys Asn Val Ser Glu Gln Ala Asn Leu
    130                 135                 140

Leu Ala Ala Lys Ile Leu Glu Ser Gln Ser Ser Leu Ser Ile His Ile
145                 150                 155                 160

Arg Arg Gly Asp Tyr Ile Lys Asn Lys Thr Ala Thr Leu Thr His Gly
                165                 170                 175

Val Cys Ser Leu Glu Tyr Tyr Lys Lys Ala Leu Asn Lys Ile Arg Asp
            180                 185                 190

Leu Ala Met Ile Arg Asp Val Phe Ile Phe Ser Asp Asp Ile Phe Trp
        195                 200                 205

Cys Lys Glu Asn Ile Glu Thr Leu Leu Ser Lys Lys Tyr Asn Ile Tyr
    210                 215                 220

Tyr Ser Glu Asp Leu Ser Gln Glu Glu Asp Leu Trp Leu Met Ser Leu
225                 230                 235                 240

Ala Asn His His Ile Ile Ala Asn Ser Ser Phe Ser Trp Trp Gly Ala
                245                 250                 255

Tyr Leu Gly Ser Ser Ala Ser Gln Ile Val Ile Tyr Pro Thr Pro Trp
            260                 265                 270

Tyr Asp Ile Thr Pro Lys Asn Thr Tyr Ile Pro Ile Val Asn His Trp
        275                 280                 285

Ile Asn Val Asp Lys His Ser Ser Cys
    290                 295

<210> SEQ ID NO 3
<211> LENGTH: 300
<212> TYPE: PRT
<213> ORGANISM: Helicobacter pylori
```

```
<400> SEQUENCE: 3

Met Ala Phe Lys Val Val Gln Ile Cys Gly Gly Leu Gly Asn Gln Met
1               5                   10                  15

Phe Gln Tyr Ala Phe Ala Lys Ser Leu Gln Lys His Leu Asn Thr Pro
            20                  25                  30

Val Leu Leu Asp Thr Thr Ser Phe Asp Trp Ser Asn Arg Lys Met Gln
        35                  40                  45

Leu Glu Leu Phe Pro Ile Asp Leu Pro Tyr Ala Asn Ala Lys Glu Ile
    50                  55                  60

Ala Ile Ala Lys Met Gln His Leu Pro Lys Leu Val Arg Asp Ala Leu
65              70                  75                  80

Lys Tyr Ile Gly Phe Asp Arg Val Ser Gln Glu Ile Val Phe Glu Tyr
                85                  90                  95

Glu Pro Lys Leu Leu Lys Pro Ser Arg Leu Thr Tyr Phe Phe Gly Tyr
            100                 105                 110

Phe Gln Asp Pro Arg Tyr Phe Asp Ala Ile Ser Ser Leu Ile Lys Gln
            115                 120                 125

Thr Phe Thr Leu Pro Pro Pro Glu Asn Asn Lys Asn Asn Asn Lys
    130                 135                 140

Lys Glu Glu Glu Tyr Gln Arg Lys Leu Ser Leu Ile Leu Ala Ala Lys
145                 150                 155                 160

Asn Ser Val Phe Val His Ile Arg Arg Gly Asp Tyr Val Gly Ile Gly
                165                 170                 175

Cys Gln Leu Gly Ile Asp Tyr Gln Lys Lys Ala Leu Glu Tyr Met Ala
            180                 185                 190

Lys Arg Val Pro Asn Met Glu Leu Phe Val Phe Cys Glu Asp Leu Lys
        195                 200                 205

Phe Thr Gln Asn Leu Asp Leu Gly Tyr Pro Phe Thr Asp Met Thr Thr
    210                 215                 220

Arg Asp Lys Glu Glu Ala Tyr Trp Asp Met Leu Leu Met Gln Ser
225                 230                 235                 240

Cys Lys His Gly Ile Ile Ala Asn Ser Thr Tyr Ser Trp Trp Ala Ala
                245                 250                 255

Tyr Leu Met Glu Asn Pro Glu Lys Ile Ile Gly Pro Lys His Trp
            260                 265                 270

Leu Phe Gly His Glu Asn Ile Leu Cys Lys Glu Trp Val Lys Ile Glu
            275                 280                 285

Ser His Phe Glu Val Lys Ser Gln Lys Tyr Asn Ala
    290                 295                 300
```

PREPARATION METHOD FOR VARIOUS NOVEL FUCOSYL OLIGOSACCHARIDES AND USE THEREOF

CROSS REFERENCE TO RELATED APPLICATIONS

This application is a National Stage of International Application No. PCT/KR2018/014000 filed Nov. 15, 2018, claiming priority based on Korean Patent Application No. 10-2017-0154840 filed Nov. 20, 2017, the disclosure of which is incorporated herein by reference in its entirety.

BACKGROUND

1. Field of the Invention

The present invention relates to a method of producing various novel fucosyl-oligosaccharides through an enzymatic reaction with α-1,2-fucosyltransferase using a GDP-L-fucose donor and various sugar acceptors, and a use thereof as a prebiotic.

2. Discussion of Related Art

Prebiotics refer to substances that are selectively fermented by beneficial intestinal bacteria to improve intestinal flora and are beneficial to human health. Recently, studies on the correlation between human diseases and intestinal flora have been reported, and intestinal flora is recognized as the second human genome, and thus research in this field is rapidly developing. In particular, as study results have been reported, showing that obesity, diabetes, and immune function are improved according to an increase in the distribution of beneficial intestinal flora, research on intestinal flora is receiving more attention.

Fucosyl-oligosaccharides are one of the main components of breast milk oligosaccharides and have activity of prebiotics selectively fermented by probiotic microorganisms and physiological activity that prevents intestinal settlement of pathogenic microorganisms. In addition to intestinal health-related physiological activity, fucosyl-oligosaccharides are known to enhance memory and are expected to help prevent dementia.

Among fucosyl-oligosaccharides, it is known that fucosylgalactose (FGal), which is a disaccharide, promotes the growth of nerve cells when hippocampal neurons, which are brain neural cells, are treated therewith. This suggests the possibility that FGal can be used as an agent for treating nervous system-related diseases such as Alzheimer's disease or Parkinson's disease.

As population aging rapidly progresses worldwide, the number of patients with neurological diseases such as Alzheimer's disease or Parkinson's disease is rapidly increasing, and accordingly, demand for developing effective therapeutic agents is increasing. For example, the global market for Alzheimer's disease therapeutics is expected to expand to $13.3 billion by 2023, and the market for Parkinson's disease therapeutics is expected to expand to $4.7 billion by 2022. However, to date, drugs for alleviating symptoms have been mainly developed, and thus there is no drug for fundamental treatment such that all demands cannot be met, and accordingly, the potential market is expected to greatly expand. In addition, the expansion of purchasing power in the third world, such as Southeast Asia, due to economic growth is expected to contribute to market growth in the future.

The above-described physiological activities of various fucosyl-oligosaccharides, such as prebiotic activity, memory enhancement, and promotion of the growth of nerve cells are expected to result from the fucose unit, and thus the inventors of the present invention produced various types of fucosyl-oligosaccharides using the enzymatic reaction of α-1,2-fucosyltransferase, which is a key enzyme involved in the fucosylation reaction and verified the characteristics thereof as prebiotics, and thus completed the present invention.

SUMMARY OF THE INVENTION

An object of the present invention is to provide a method of producing various fucosyl-oligosaccharides through the enzymatic reaction of α-1,2-fucosyltransferase with a GDP-L-fucose donor and various sugar acceptors.

Another object of the present invention is to provide a use of fucosyl-oligosaccharides having prebiotic properties.

According to an aspect of the present invention, there is provided a prebiotic pharmaceutical composition including one or more fucosyl-oligosaccharides selected from the group consisting of 2'-fucosylglucose, 2'-fucosylgalactose, 2'-fucosylcellobiose, 2'-fucosylfructose, 2'-fucosylsucrose, 2'-fucosylmaltose, 2'-fucosylmannose, 2'-fucosylxylose, and 2'-fucosylagarobiose.

The present invention also provides a method of improving the intestinal health of a subject, including administering the prebiotic pharmaceutical composition to the subject.

The present invention also provides a prebiotic cosmetic composition including one or more fucosyl-oligosaccharides selected from the group consisting of 2'-fucosylglucose, 2'-fucosylgalactose, 2'-fucosylcellobiose, 2'-fucosylfructose, 2'-fucosylsucrose, 2'-fucosylmaltose, 2'-fucosylmannose, 2'-fucosylxylose, and 2'-fucosylagarobiose.

The present invention also relates to a prebiotic food composition including one or more fucosyl-oligosaccharides selected from the group consisting of 2'-fucosylglucose, 2'-fucosylgalactose, 2'-fucosylcellobiose, 2'-fucosylfructose, 2'-fucosylsucrose, 2'-fucosylmaltose, 2'-fucosylmannose, 2'-fucosylxylose, and 2'-fucosylagarobiose.

The present invention also provides a method of producing a fucosyl-oligosaccharide, including reacting a sugar acceptor and a guanosine 5'-diphospho-β-L-fucose (GDP-L-fucose) donor with α-1,2-fucosyltransferase to produce a fucosyl-oligosaccharide, wherein the sugar acceptor includes one or more selected from the group consisting of glucose, galactose, cellobiose, lactose, fructose, sucrose, maltose, mannose, xylose, and agarobiose, and the α-1,2-fucosyltransferase includes any one selected from the amino acid sequences of SEQ ID NOS: 1 to 3.

The present invention also provides a method of producing a fucosyl-oligosaccharide, including: culturing, in the presence of a sugar acceptor and glycerol, recombinant *E. coli* or yeast into which a vector for expressing ManB, ManC, Gmd, and WcaG involved in the de novo pathway for producing a guanosine 5'-diphospho-β-L-fucose (GDP-L-fucose) donor; and a vector for expressing α-1,2-fucosyltransferase are introduced; and separating and purifying a fucosyl-oligosaccharide from the *E. coli* culture, wherein the sugar acceptor includes one or more selected from the group consisting of glucose, galactose, cellobiose, lactose, fructose, sucrose, maltose, mannose, xylose, and agarobiose, and the α-1,2-fucosyltransferase includes any one selected from the amino acid sequences of SEQ ID NOS: 1 to 3.

The present invention has the effect of providing a method of producing a fucosyl-oligosaccharide using the enzymatic reaction of a GDP-L-fucose donor and various sugar acceptors with α-1,2-fucosyltransferase or by applying the enzymatic reaction to a metabolic engineering technique in recombinant *E. coli*.

The present invention also provides the effect of fucosyl-oligosaccharides to be used as prebiotic materials in medical, cosmetic, and food fields based on the prebiotic properties thereof.

DETAILED DESCRIPTION OF EXEMPLARY EMBODIMENTS

Figure 1:
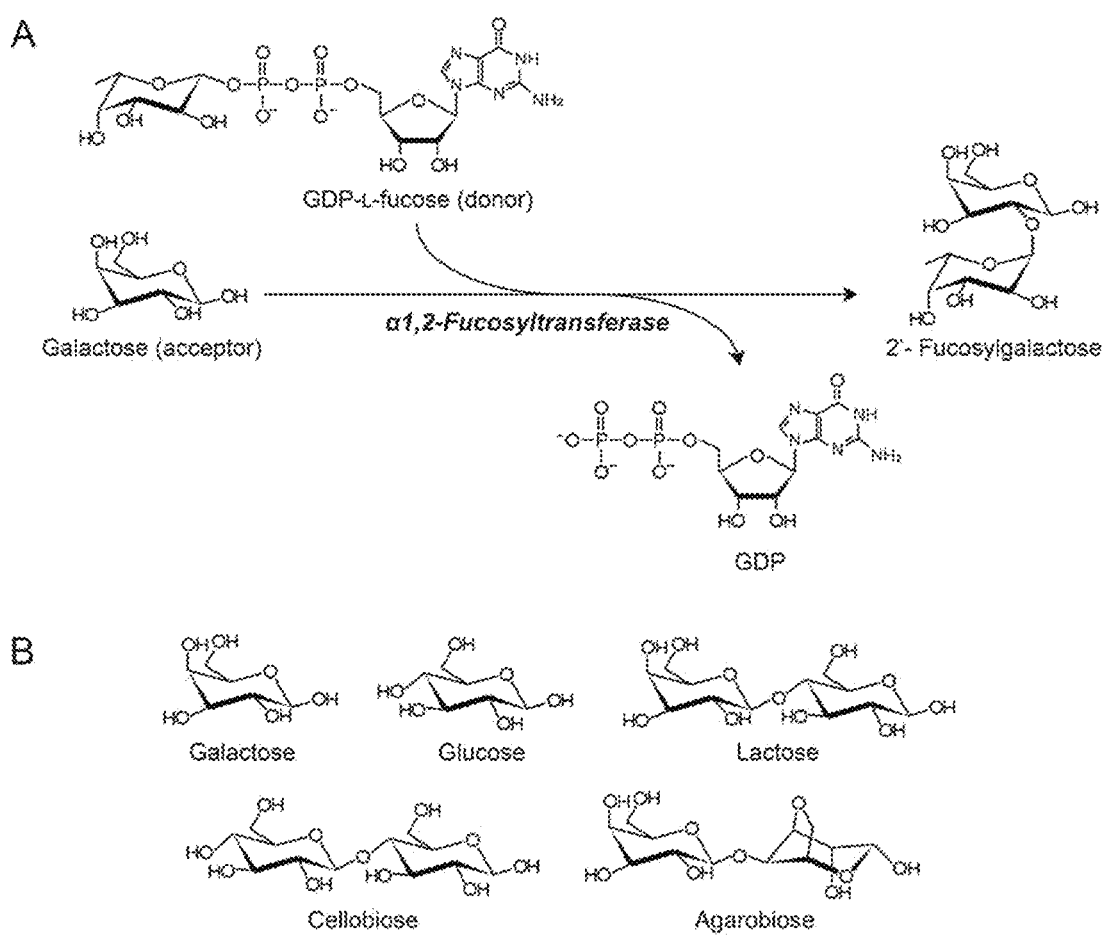
FIG. 1 is a view illustrating the production of various types of fucosyl-oligosaccharides using a GDP-fucose donor and various sugar acceptors through the enzymatic reaction of α-1,2-fucosyltransferase.

The inventors of the present invention first produced fucosylgalactose (FGal) (U.S. Pat. No. 7,858,578), which has been produced only by chemical synthesis until now, through an enzymatic reaction and microbial fermentation. In addition, the inventors first proved that FGal is a prebiotic fermented by Bifidobacter, which is a probiotic microorganism. In particular, among various sugar acceptors, agarobiose, which is a disaccharide basic structure constituting agarose, a major carbohydrate of red algae, was used to first produce 2-fucosylagarobiose. Agarobiose is known as a bioactive substance with antioxidant, antimicrobial, anti-inflammatory, and anticancer effects, and 2-fucosylagarobiose produced through the fucosylation reaction is a new material and is also expected to be a material with various physiological activities.

Therefore, the present invention relates to a prebiotic pharmaceutical composition including one or more fucosyl-oligosaccharides selected from the group consisting of 2'-fucosylglucose, 2'-fucosylgalactose, 2'-fucosylcellobiose, 2'-fucosylfructose, 2'-fucosylsucrose, 2'-fucosylmaltose, 2'-fucosylmannose, 2'-fucosylxylose, and 2'-fucosylagarobiose.

The fucosyl-oligosaccharide(s) are prebiotics that promote the proliferation of beneficial intestinal bacteria, inhibit the growth of harmful intestinal bacteria, and are not metabolized by pathogenic microorganisms. In addition, by binding to the adhesion sites or receptor sites of *Salmonella*, *Helicobacter*, Pathogenic *E. coli*, Norovirus, and the like, the fucosyl-oligosaccharide(s) may also prevent pathogenic bacteria and viruses from infecting the human body and proliferating. Thereamong, 2-fucosylgalactose may be used as a therapeutic agent for neurodegenerative diseases such as Parkinson's disease and Alzheimer's disease through promotion of the growth of nerve cells, and 2-fucosylagarobiose can also be used as antioxidant, antibacterial, anti-inflammatory, and anticancer agents due to properties of agarobiose itself, such as antioxidant, antibacterial, anti-inflammatory, and anticancer properties.

According to one embodiment of the present invention, *Bifidobacterium longum* subsp. *infantis* ATCC 15697 decomposes 2-fucosylgalactose into galactose and fucose through intracellular fucosidase and uses both, and *Bifidobacterium bifidum* DSM 20082 extracellularly decomposes 2-fucosylgalactose into galactose and fucose, and then uses only galactose. In addition, it can be seen that *E. coli*, which causes urinary tract infections, neonatal meningitis, and septicemia, and *Salmonella enterica* serovar *typhimurium*, which causes diarrhea and bacteremia, are unable to metabolize 2-fucosylgalactose and are prebiotics selectively fermented only by probiotic microorganisms.

The fucosyl-oligosaccharide(s) may be produced by reacting a sugar acceptor and a guanosine 5'-diphospho-β-L-fucose (GDP-L-fucose) donor with α-1,2-fucosyltransferase. Alternatively, recombinant *E. coli* or yeast into which a vector for expressing ManB, ManC, Gmd, and WcaG involved in the de novo pathway for producing GDP-L-fucose; and a vector for expressing α-1,2-fucosyltransferase are introduced may be cultured in the presence of a sugar acceptor and glycerol, respectively, and fucosyl-oligosaccharide(s) may be obtained from the culture by separation and purification.

As used herein, the term "beneficial intestinal bacteria" has the same meaning as "probiotics" and refers to strains that have a beneficial effect on the intestinal environment when ingested and reaching the intestine, and means bacteria that survive in stomach acid and bile acid to reach the small intestine and consequently, proliferate and settle in the intestine, have a beneficial effect in the intestinal tract, and satisfy conditions such as no toxicity and non-pathogenicity. For example, the beneficial intestinal bacteria include bacteria belonging to the genus *Lactobacillus*, the genus *Lactococcus*, the genus *Enterococcus*, the genus *Streptococcus*, and the genus *Bifidobacterium*. In particular, the beneficial intestinal bacteria are strains belonging to the genus *Bifidobacterium*, the genus *Lactobacillus*, or the genus *Streptococcus*, more particularly strains belonging to the genus *Bifidobacterium* or the genus *Streptococcus*. Still more particularly, the strain belonging to the genus *Bifidobacterium* according to the present invention includes *Bifidobacterium longum* subsp. *infantis* ATCC 15697, *Bifidobacterium bifidum* DSM 20082, or *Bifidobacterium kashiwanohence* DSM 21854. The strain belonging to the genus *Lactobacillus* includes *Lactobacillus reuteri*, and the strain belonging to the genus *Streptococcus* includes *Streptococcus thermophilus*.

As used herein, the term "harmful intestinal bacteria" refers to strains that have an adverse effect on the intestinal environment when ingested and reaching the intestine. For example, the harmful intestinal bacteria include strains belonging to the genus *Pseudomonas-aeruginosa*, the genus *Vibrio*, the genus *Staphylococcus*, the genus *Clostridium perfringens*, the genus *Eubacterium*, and the genus *Bacteroides*, and sulfate reducers. Particularly, the harmful intestinal bacteria are strains belonging to the genus *Clostridium perfringens*, the genus *Eubacterium*, or the genus *Bacteroides*. More particularly, the strain belonging to the genus *Clostridium perfringens* includes *Clostridium difficile* or *Clostridium perfringens*. The strain belonging to the genus *Eubacterium* includes *Eubacterium limosum*, and the strain belonging to the genus *Bacteroides* includes *Bacteroides fragilis*.

The prebiotic pharmaceutical composition of the present invention may further include a pharmaceutically acceptable carrier.

The pharmaceutically acceptable carrier includes carriers and vehicles commonly used in the medical field, and particularly, includes ion exchange resins, alumina, aluminum stearate, lecithin, serum proteins (e.g., human serum albumin), buffer substances (e.g., various phosphates, glycine, sorbic acid, potassium sorbate, and partial glyceride mixtures of saturated vegetable fatty acids), water, salts or electrolytes (e.g., protamine sulfate, disodium hydrogen phosphate, potassium hydrogen phosphate, sodium chloride, and zinc salts), colloidal silica, magnesium trisilicate, polyvinyl pyrrolidone, cellulose-based substrates, polyethylene glycol, sodium carboxymethylcellulose, polyarylates, wax, polyethylene glycol, or lanolin, but the present invention is not limited thereto.

In addition, the prebiotic pharmaceutical composition of the present invention may further include, in addition to the above-described ingredients, a lubricant, a wetting agent, an emulsifying agent, a suspension agent, a preservative, or the like.

In one embodiment, the prebiotic pharmaceutical composition of the present invention may be formulated and used in the form of various preparations suitable for oral administration or parenteral administration.

Non-limiting examples of the preparations for oral administration include troches, lozenges, tablets, aqueous suspensions, oily suspensions, prepared powders, emulsions, hard capsules, soft capsules, syrups, and elixirs.

To formulate the prebiotic pharmaceutical composition of the present invention for oral administration, a binder such as lactose, saccharose, sorbitol, mannitol, starch, amylopectin, cellulose, gelatin, or the like; an excipient such as dicalcium phosphate or the like; a disintegrant such as corn starch, sweet potato starch, or the like; a lubricant such as magnesium stearate, calcium stearate, sodium stearyl fumarate, polyethylene glycol wax, or the like; or the like may be used, and a sweetener, a fragrance, syrup, or the like may also be used.

Furthermore, in the case of capsules, a liquid carrier such as a fatty oil, and the like may be further used in addition to the aforementioned materials.

Non-limiting examples of the preparations for parenteral administration may include injections, suppositories, respiratory inhalation powders, spray aerosols, oral sprays, mouthwashes, toothpastes, ointments, powders for application, oils, and creams.

To formulate the prebiotic pharmaceutical composition of the present invention to be used for parenteral administration, sterilized aqueous solutions, non-aqueous solvents, suspensions, emulsions, freeze-dried preparations, agents for external application, or the like may be used, and as the non-aqueous solvents and the suspensions, propylene glycol, polyethylene glycol, a vegetable oil such as olive oil, an injectable ester such as ethyl oleate, or the like may be used.

In addition, more particularly, when the prebiotic pharmaceutical composition of the present invention is formulated into an injection, the prebiotic pharmaceutical composition of the present invention is mixed with a stabilizer or a buffer in water to prepare a solution or a suspension, followed by preparation into an ampoule or vial unit dosage form. In addition, when the pharmaceutical composition of the present invention is formulated into an aerosol, a propellant or the like for dispersing a water-dispersed concentrate or wet powder may be blended with an additive.

In addition, when the prebiotic pharmaceutical composition of the present invention is formulated into an ointment, a cream, or the like, animal oil, vegetable oil, wax, paraffin, starch, tragacanth, a cellulose derivative, polyethylene glycol, silicon, bentonite, silica, talc, zinc oxide, or the like may be used as a carrier.

A pharmaceutically effective amount and effective dosage level of the prebiotic pharmaceutical composition of the present invention may vary depending on formulation methods, administration methods, administration time, and/or administration route of the composition, and may vary depending on various factors including the type and degree of reaction to be achieved via administration of the prebiotic pharmaceutical composition of the present invention, the type, age, and body weight of an individual to which the composition is administered, general health condition, the symptoms or severity of disease, gender, diet, excretion, drugs used simultaneously or at different times in the corresponding individual, components of other compositions, and the like, and similar factors well known in the medical field, and one of ordinary skill in the art can determine and prescribe an effective dose for targeted treatment. The prebiotic pharmaceutical composition of the present invention may be administered once a day or in multiple doses. Thus, the effective dose is not intended to limit the scope of the present invention in any way.

The administration route and administration method of the prebiotic pharmaceutical composition of the present invention may be independent from each other, the administration method is not particularly limited, and the administration route and the administration method may be an arbitrary administration route and administration route as long as they enable the prebiotic pharmaceutical composition to reach the corresponding site. The prebiotic pharmaceutical composition may be administered orally or parenterally.

The parenteral administration may be, for example, intravenous administration, intraperitoneal administration, intramuscular administration, transdermal administration, subcutaneous administration, or the like, and the prebiotic pharmaceutical composition may be applied or sprayed on a diseased site, or inhaled, but the present invention is not limited thereto.

The prebiotic pharmaceutical composition of the present invention may preferably be administered orally or by injection.

The present invention also provides a method of improving the intestinal health of a subject, including administering the prebiotic pharmaceutical composition to the subject.

The method of improving the intestinal health according to the present invention includes treating heartburn, indigestion, abdominal bloating, diarrhea, constipation, gas, or the like.

As used herein, the term "subject" means all animals including mammals including mice, livestock, humans, and the like.

In the method of improving the intestinal health according to the present invention, detailed descriptions of the dosage, administration route, administration method, and the like of the prebiotic pharmaceutical composition are the same as those described above with respect to the pharmaceutical composition.

The present invention also provides a prebiotic cosmetic composition including one or more fucosyl-oligosaccharides selected from the group consisting of 2'-fucosylglucose, 2'-fucosylgalactose, 2'-fucosylcellobiose, 2'-fucosylfructose, 2'-fucosylsucrose, 2'-fucosylmaltose, 2'-fucosylmannose, 2'-fucosylxylose, and 2'-fucosylagarobiose.

Oligosaccharides including fucose may exhibit functionality that thickens the skin epidermal layer to alleviate wrinkles. Therefore, in consideration of skin permeability and absorption rate, fucosyl-oligosaccharides may exhibit excellent anti-wrinkle activity. Among the fucosyl-oligosaccharides, 2'-fucosylagarobiose can be effectively used to inhibit or treat atopy, acne, dandruff, and the like through the antioxidant and antibacterial activities of agarobiose itself.

The cosmetic composition of the present invention includes: water-soluble vitamins such as vitamin B1, vitamin B2, vitamin B6, pyridoxine, pyridoxine hydrochloride, vitamin B12, pantothenic acid, nicotinic acid, nicotinic acid amide, folic acid, vitamin C, vitamin H, and the like; oil-soluble vitamins such as vitamin A, carotene, vitamin D2, vitamin D3, vitamin E (d1-alpha tocopherol, d-alpha tocopherol, d-alpha tocopherol), and the like; polymer peptides such as collagen, hydrolyzed collagen, gelatin, elastin, hydrolyzed elastin, keratin, and the like; polymeric polysaccharides such as hydroxyethyl cellulose, xanthan gum, sodium hyaluronate, chondroitin sulfate or salts thereof (sodium salts and the like), and the like; sphingolipids such as ceramide, phytosphingosine, sphingosaccharide lipid, and the like; or seaweed extracts such as a brown algae extract, a red algae extract, a green algae extract, and the like.

The cosmetic composition of the present invention may include, in addition to the above essential ingredients, other ingredients mixed in general cosmetics as necessary. Other mixed ingredients that may be added may include oil and fat ingredients, a moisturizing agent, an emollient agent, a surfactant, organic and inorganic pigments, organic powders, an ultraviolet absorbent, a preservative, a bactericide, an antioxidant, a plant extract, a pH adjusting agent, alcohols, dyes, pigments, a blood circulation promoter, a cooling agent, an antiperspirant, purified water, and the like. Oil and fat ingredients may include ester-based oil and fat, hydrocarbon-based oil and fat, silicone-based oil and fat, fluorine-based oil and fat, animal oil and fat, vegetable oil and fat, and the like.

In addition, other mixed ingredients that may be added are not limited to the above examples, and may be mixed within a range that does not adversely affect the objects and effects of the present invention.

The cosmetic composition of the present invention may be in the form of a solution, an emulsion, a viscous mixture, or the like.

The ingredients included in the cosmetic composition of the present invention may include ingredients commonly used in cosmetic compositions as active ingredients, and include, for example, general adjuvants and carriers such as a stabilizer, a solubilizer, vitamins, a pigment, and a flavor.

The cosmetic composition of the present invention may be prepared into any form generally prepared in the art, and examples thereof include a skin lotion, a skin softener, a skin toner, a milk lotion, an astringent, a lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a hair lotion, a hair tonic, a hair essence, a hair shampoo, a hair rinse, a hair treatment, a body lotion, and a body cleanser.

The present invention also provides a prebiotic food composition including one or more fucosyl-oligosaccharides selected from the group consisting of 2'-fucosylglucose, 2'-fucosylgalactose, 2'-fucosylcellobiose, 2'-fucosylfructose, 2'-fucosylsucrose, 2'-fucosylmaltose, 2'-fucosylmannose, 2'-fucosylxylose, and 2'-fucosylagarobiose.

The food composition of the present invention may be used as a health functional food, a food additive, or a dietary supplement.

When used as a food additive, the fucosyl-oligosaccharide(s) may be appropriately used according to a general method such as being added directly or mixed in combination with other foods or food ingredients.

In addition, the amount of fucosyl-oligosaccharide(s) to be mixed may be appropriately changed according to the purpose of use (prevention, health or therapeutic treatment), and ranges from preferably 0.01 wt % to 95 wt %, more preferably 0.1 wt % to 80 wt %, with respect to a total weight of the food composition. When the amount is less than 0.01 wt %, dose efficiency may be lowered, and when the amount is greater than 95 wt %, there may be difficulties in formulation.

Specifically, when prepared into a food or a beverage, the fucosyl-oligosaccharide(s) of the present invention are added in an amount of 15 wt % or less, preferably 10 wt % or less, with respect to a total weight of raw materials. However, in the case of long-term ingestion for health and hygienic purposes or for health control purposes, the amount may be below the above range, and since there is no problem in terms of safety, the active ingredient may also be used in an amount above the above range.

The type of the food is not particularly limited, but examples of foods to which the fucosyl-oligosaccharide(s) of the present invention may be added include meats, sausages, bread, chocolates, candies, snacks, confectionaries, pizzas, instant noodles, other noodles, gums, dairy products including ice creams, various kinds of soup, beverages, teas, drinks, alcoholic drinks, vitamin complexes, and the like, and all health foods in the ordinary sense are included.

When the food composition of the present invention is prepared as a beverage, the food composition may include additional ingredients such as various flavor enhancers or natural carbohydrates like general beverages. As the natural carbohydrates, monosaccharides such as glucose and fructose; disaccharides such as maltose and sucrose; natural sweeteners such as dextrin and cyclodextrin; and synthetic sweeteners such as saccharin and aspartame may be used. The natural carbohydrate is included in an amount of 0.01 wt % to 10 wt %, preferably 0.01 wt % to 0.1 wt %, with respect to the total weight of the food composition of the present invention.

The food composition of the present invention may include various nutritional supplements, vitamins, electrolytes, flavors, colorants, pectic acid and salts thereof, alginic acid and salts thereof, organic acids, a protective colloid thickener, a pH adjuster, a stabilizer, a preservative, glycerin, alcohols, a carbonating agent used in carbonated beverages, and the like, and may include flesh for the preparation of natural fruit juice, fruit juice beverages, and vegetable beverages, but the present invention is not limited thereto. These ingredients may be used alone or a combination thereof may be used. The proportion of these additives is not particularly limited, but may range from 0.01 wt % to 0.1 wt % with respect to the total weight of the food composition of the present invention.

In the case of long-term ingestion for health and hygienic purposes or for health control purposes, the food composition of the present invention may be ingested for a long period of time since there is no problem in terms of safety.

The present invention also provides a method of producing a fucosyl-oligosaccharide, including reacting a sugar acceptor and a guanosine 5'-diphospho-β-L-fucose (GDP-L-fucose) donor with α-1,2-fucosyltransferase to produce a fucosyl-oligosaccharide, wherein the sugar acceptor includes one or more selected from the group consisting of glucose, galactose, cellobiose, lactose, fructose, sucrose, maltose, mannose, xylose, and agarobiose, and the α-1,2-fucosyltransferase includes any one selected from the amino acid sequences of SEQ ID NOS: 1 to 3.

As a conventional method for producing fucosyl-oligosaccharides, chemical synthesis of 2-fucosylgalactose is known, but this method has a complicated synthesis process and uses organic solvents such as pyridine, acetic acid, dichloromethane, and toluene, and even after many processes, synthesis was possible only in a derivatized form, not 2-fucosylgalactose (Kalovidouris S A et al. *J Ame Chem Soc* 127: 1340-1341 (2005)).

However, in the method of producing a fucosyl-oligosaccharide according to the present invention, by reacting a sugar acceptor and a GDP-L-fucose donor with α-1,2-fucosyltransferase, a fucosyl-oligosaccharide, not a derivatized form, can be produced. In addition, it is possible to produce various types of fucosyl-oligosaccharides using various sugar acceptors (see FIG. 1).

The sugar acceptor may be selected from the group consisting of glucose, galactose, cellobiose, lactose, fructose, sucrose, maltose, mannose, xylose, and agarobiose.

The α-1,2-fucosyltransferase may be derived from *Helicobacter pylori*, *Bacteroides fragilis*, *E. coli* O126, or the like, and particularly, may include any one selected from the amino acid sequences of SEQ ID NOS: 1 to 3.

According to one embodiment of the present invention, the α-1,2-fucosyltransferase showed a difference in reactivity according to the type of sugar acceptor. For example, *Bacteroides fragilis*-derived WcfB exhibited high activity for cellobiose, galactose, and glucose, *E. coli* O126-derived WbgL exhibited high activity for lactose and galactose, and *Helicobacter pylori*-derived FucT2 exhibited high activity for cellobiose and galactose.

The enzymatic reaction of the sugar acceptor and the GDP-L-fucose donor with α-1,2-fucosyltransferase may be performed at 20° C. to 40° C. for 3 hours to 24 hours, more particularly at 25° C. to 35° C. for 6 hours to 12 hours.

A fucosyl-oligosaccharide produced by the method of producing a fucosyl-oligosaccharide according to the present invention may be 2'-fucosylglucose, 2'-fucosylgalactose, 2'-fucosylcellobiose, 2'-fucosyllactose, 2'-fucosylfructose, 2'-fucosylsucrose, 2'-fucosylmaltose, 2'-fucosylmannose, 2'-fucosylxylose, or 2'-fucosylagarobiose.

The present invention also provides a method of producing a fucosyl-oligosaccharide, including: culturing, in the presence of a sugar acceptor and glycerol, recombinant *E. coli* or yeast into which a vector for expressing ManB, ManC, Gmd, and WcaG involved in the de novo pathway for producing a guanosine 5'-diphospho-β-L-fucose (GDP-L-fucose) donor; and a vector for expressing α-1,2-fucosyltransferase are introduced; and separating and purifying a fucosyl-oligosaccharide from the *E. coli* culture, wherein the sugar acceptor includes one or more selected from the group consisting of glucose, galactose, cellobiose, lactose, fructose, sucrose, maltose, mannose, xylose, and agarobiose, and the α-1,2-fucosyltransferase includes any one selected from the amino acid sequences of SEQ ID NOS: 1 to 3.

According to a method of producing 2-fucosyllactose, which is a fucosyl-oligosaccharide, through fermentation by employing a conventional microorganism metabolic engineering technique, 2-fucosyllactose is produced from lactose using *Helicobacter*-derived fucosyltransferase, but it is disadvantageous in that it is not possible to produce various fucosyl-oligosaccharides.

In contrast, according to the method of producing a fucosyl-oligosaccharide according to the present invention, various types of fucosyl-oligosaccharides may be produced through microbial fermentation by employing a microorganism metabolic engineering technique, and to this end, *E. coli* or yeast in which the metabolic pathway of a material used as a sugar acceptor is deleted is used as a host, the de novo pathway is introduced into the host to produce GDP-1-fucose as a donor, a sugar substance is supplied as an acceptor, glycerol is used as a carbon source, and α-1,2-fucosyltransferase is introduced, thereby producing fucosyl-oligosaccharides through fermentation. Therefore, the method of the present invention may include:

constructing a vector for expressing ManB, ManC, Gmd, and WcaG involved in the de novo pathway for producing, as a donor, guanosine 5'-diphospho-β-L-fucose (GDP-L-fucose) in *E. coli*, and a vector for expressing α-1,2-fucosyltransferase;

introducing the vectors into *E. coli* or a yeast in which the metabolic pathway of a material used as a sugar acceptor is deleted to transform the *E. coli* or yeast;

culturing the transformed *E. coli* or yeast using glycerol as a carbon source in the presence of a sugar acceptor; and separating and purifying a fucosyl-oligosaccharide from the culture.

The de novo pathway for producing GDP-L-fucose is a pathway in which, by using fructose 6P as a starting material and mannose-6-phosphate isomerase (ManM), phosphomannomutase (ManB), mannose-1-phosphate guanosyltransferase (ManC), GDP-mannose-4,6-dehydratase (Gmd), and GDP-L-fucose synthase (WcaG), intermediate products such as mannose 6P, mannose 1P, GDP-D-mannose, and GDP-4-keto-6-deoxymannose are sequentially produced, and finally, GDP-L-fucose is produced.

The culture of the transformed *E. coli* may include fed-batch culture.

The fed-batch culture may be performed at 25° C. to 37° C. for 2 hours to 60 hours, and isopropyl β-D-1-thiogalactopyranoside (IPTG) may be added and the fed-batch culture may be performed at 20° C. to 30° C. for 60 hours to 150 hours.

Hereinafter, the present invention will be described in further detail with reference to the following examples, but these examples are not intended to limit the scope of the present invention.

<Example 1> Synthesis of Fucosyl-Oligosaccharides

To produce various fucosyl-oligosaccharides, the enzymatic reaction of α-1,2-fucosyltransferase under conditions of a GDP-fucose donor and various sugar acceptors was performed (see FIG. 1).

As the α-1,2-fucosyltransferases, E. coli-derived WbgL (GenBank: ABE98421.1), Helicobacter pylori-derived FucT2 (GenBank: AAC99764.1), and WcfB (GenBank: AAD40713.1) derived from Bacteroides fragilis, which is an intestinal bacterium, were used. A pET21a plasmid vector containing a gene encoding each enzyme was transformed into E. coli BL21 (DE3) Star. Each recombinant E. coli was cultured at 37° C. and 250 rpm until OD 0.5, and then enzyme expression was induced at 16° C. and 250 rpm for 18 hours using 0.1 mM IPTG.

FIG. 1 illustrates a view for producing various types of fucosyl-oligosaccharides using a GDP-fucose donor and various sugar acceptors through the enzymatic reaction of α-1,2-fucosyltransferase, in which an experiment for reactivity thereof was conducted using sugar acceptors such as glucose, galactose, cellobiose, lactose, fructose, sucrose, maltose, mannose, xylose, and agarobiose.

To produce agarobiose, acid hydrolysis of agarose was performed. 10% (w/w) agarose was subjected to an acid hydrolysis reaction using 2% phosphoric acid at 90° C. for 3 hours. After the acid hydrolysis, calcium hydroxide was added to the reaction solution to neutralize and remove phosphoric acid.

An experiment for enzymatic reactivity between the α-1,2-fucosyltransferases and various sugar acceptors was conducted as follows. A 2 mM GDP-fucose donor, 5 mM of each sugar acceptor, 1 mM 1,4-dithiothreitol (DTT), 50 mM Tris-HCl (pH 7.0), and 5 mg/mL of an intracellular crude enzyme solution of E. coli expressing WbgL, FucT2, or WcfB were allowed to react at 30° C. and 600 rpm for 12 hours.

Figure 2:
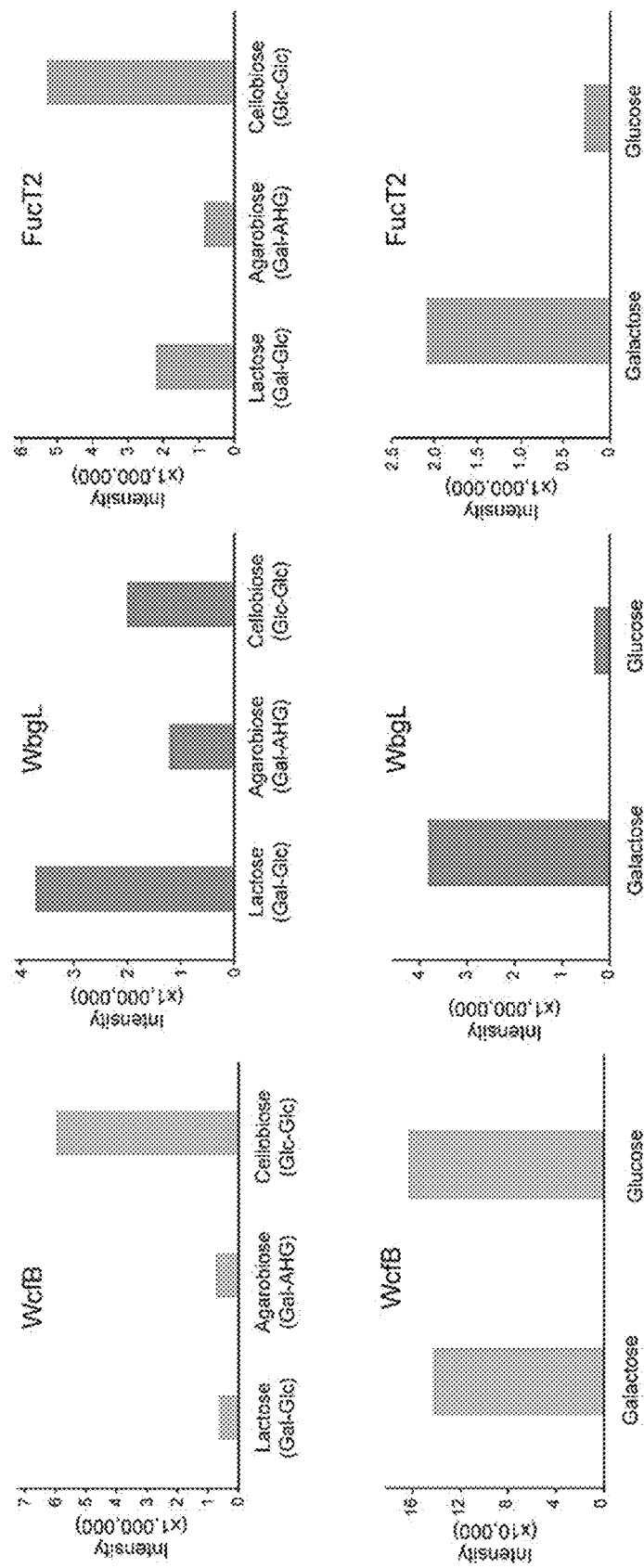
FIG. 2 illustrates test results showing the reactivity between α-1,2-fucosyltransferase and various sugar acceptors.

As shown in FIG. 2, Bacteroides fragilis-derived WcfB exhibited high activity for cellobiose, galactose, and glucose, E. coli O126-derived WbgL exhibited high activity for lactose and galactose, and Helicobacter pylori-derived FucT2 exhibited high activity for cellobiose and galactose.

<Example 2> Enzymatic Reaction of α-1,2-Fucosyltransferase for Various Sugar Acceptors A fucosyl-oligosaccharide was produced using a GDP-fucose donor and galactose or glucose as an acceptor through the enzymatic reaction of WbgL, which is α-1,2-fucosyltransferase. The sugar acceptors used in the enzymatic reaction were glucose, galactose, cellobiose, lactose, fructose, sucrose, maltose, mannose, xylose, and agarobiose. Enzymatic reaction conditions were as follows: 1 mg/mL of an intracellular crude enzyme solution of each recombinant E. coli, a 0.2 mM GDP-fucose donor, a 0.5 mM sugar acceptor, and a 20 mM sodium phosphate buffer (pH 6.0) were used to allow an enzymatic reaction at 30° C. for 12 hours. The reaction products were subjected to LC/MS analysis to confirm exact mass values. In the LC/MS analysis, a Thermo Hypercarb porous graphitic carbon LC column (Thermo Fisher Scientific) was used, and a positive ion mode was used. Two mobile phases such as a 25 µM lithium chloride solution as mobile phase A and a 100% acetonitrile solution as mobile phase B were flowed at a rate of 0.2 mL/min with a gradient of 0% to 80% for 41 minutes. At this time, the temperature of the column was maintained at 70° C. Source-dependent parameters were as follows: nebulizing gas flow, 1.5 L/min; interface voltage, 4.5 kV; detector voltage, 1.65 kV; a curved desolvation line (CDL) temperature, 200° C.; and heat block temperature, 200° C. The MS analysis was performed in the range of 100 m/z to 700 m/z.

Figure 3:
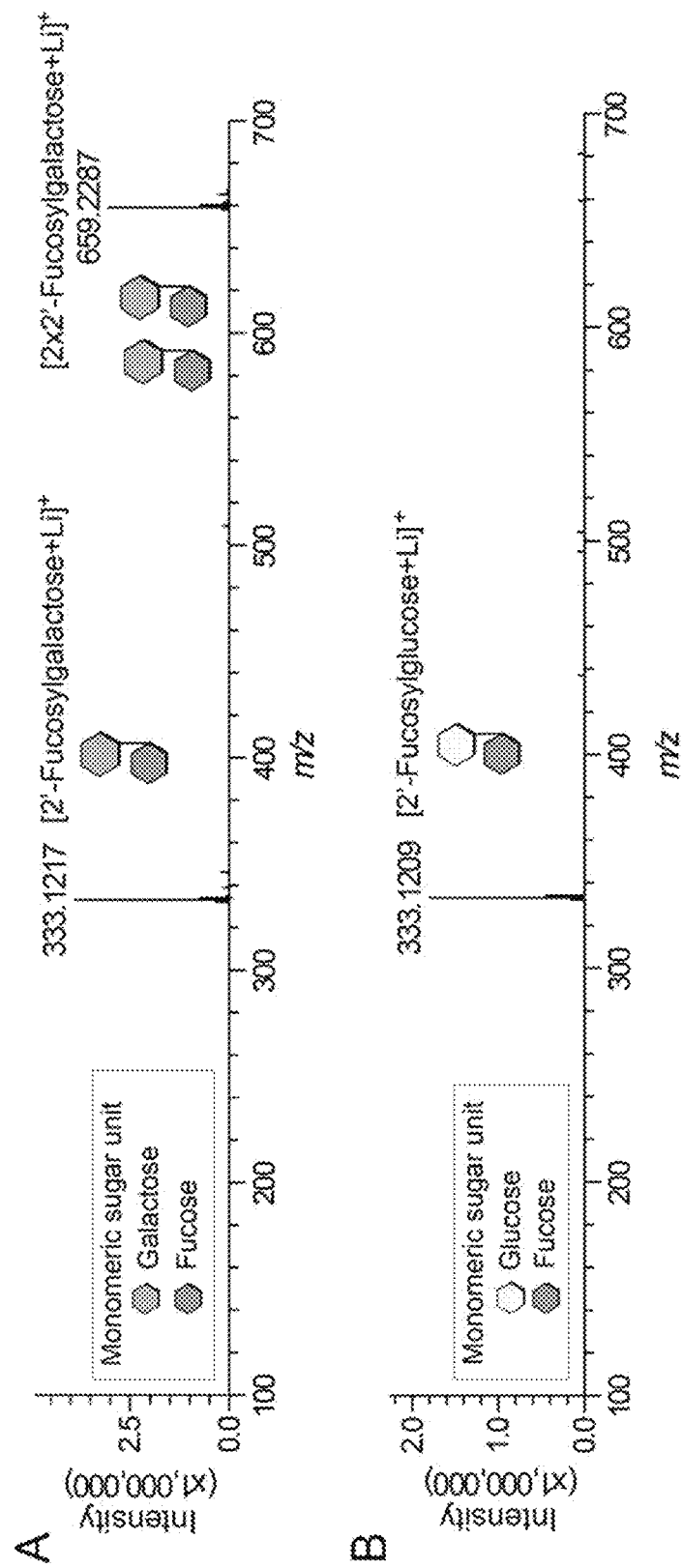
FIGS. 3 to 5 illustrate LC/MS analysis results of fucosyl-oligosaccharides produced through the enzymatic reaction with α-1,2-fucosyltransferase using a GDP-L-fucose donor and sugar acceptors such as glucose, galactose, cellobiose, lactose, fructose, sucrose, maltose, mannose, xylose, and agarobiose.
Figure 4:
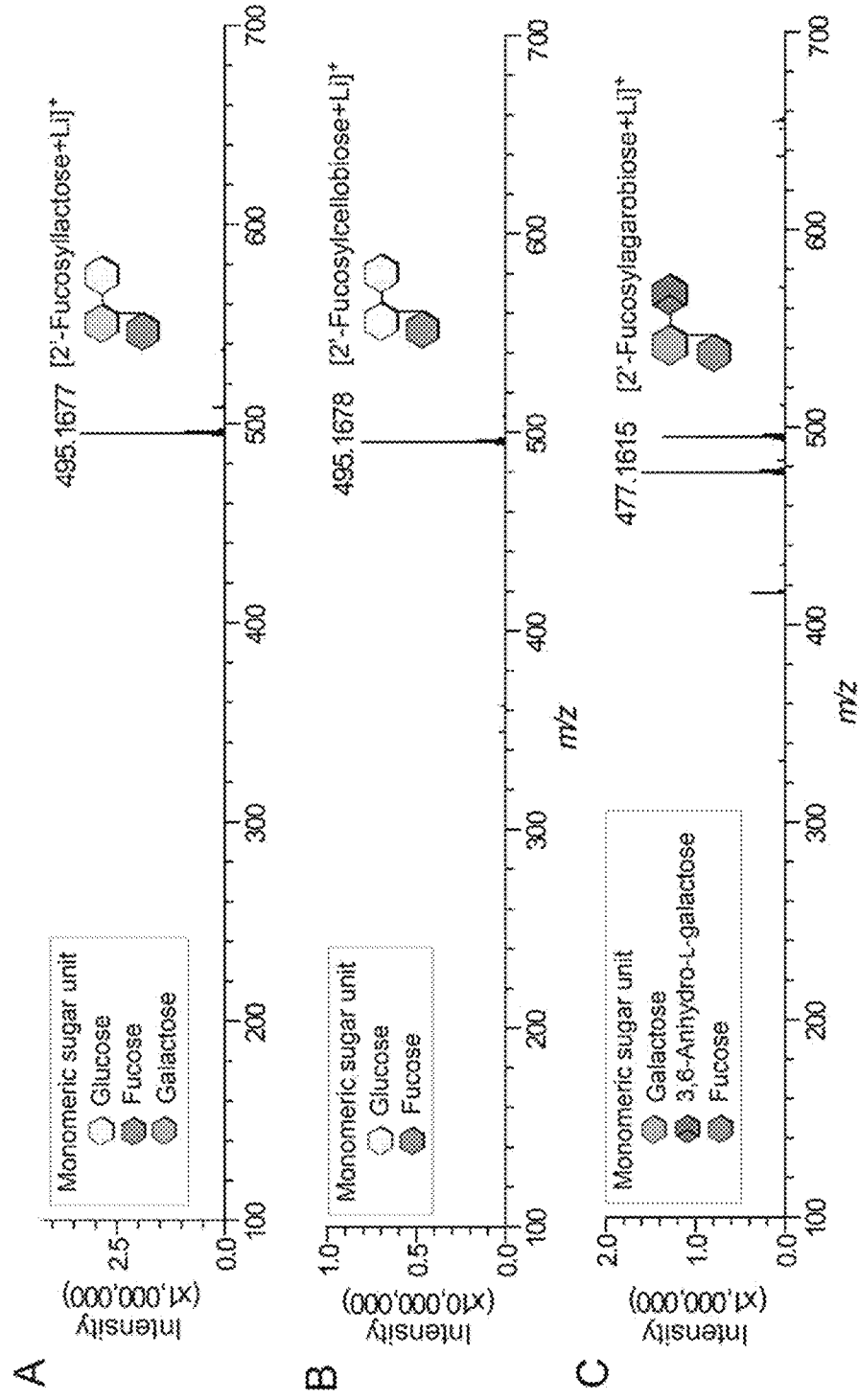
Figure 5:
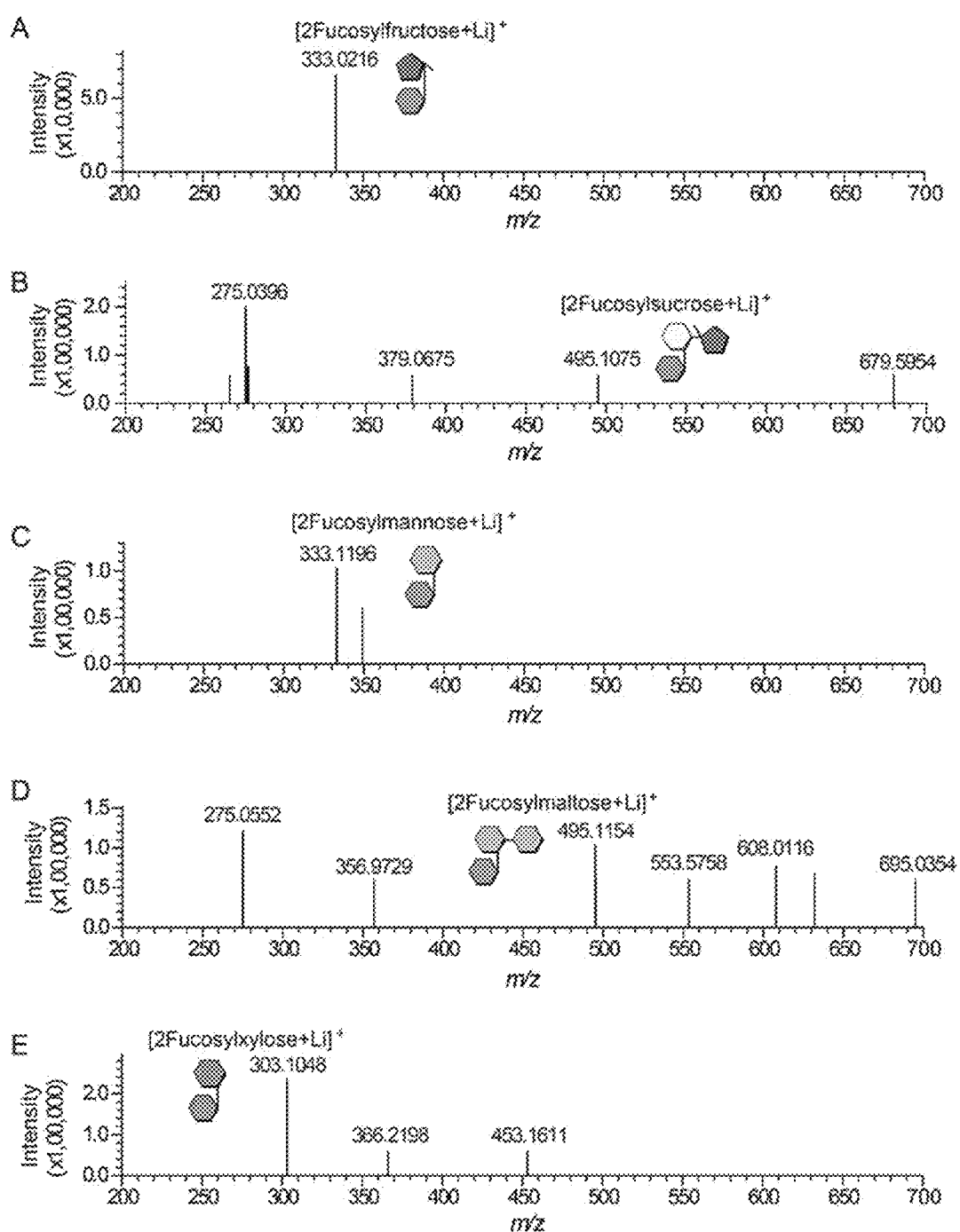

As illustrated in FIGS. 3 to 5, it was confirmed that, for each sugar acceptor, 2'-fucosylglucose, 2'-fucosylgalactose, 2'-fucosylcellobiose, 2'-fucosyllactose, 2'-fucosylfructose, 2'-fucosylsucrose, 2'-fucosylmaltose, 2'-fucosylmannose, 2'-fucosylxylose, or 2'-fucosylagarobiose were produced.

Figure 6:
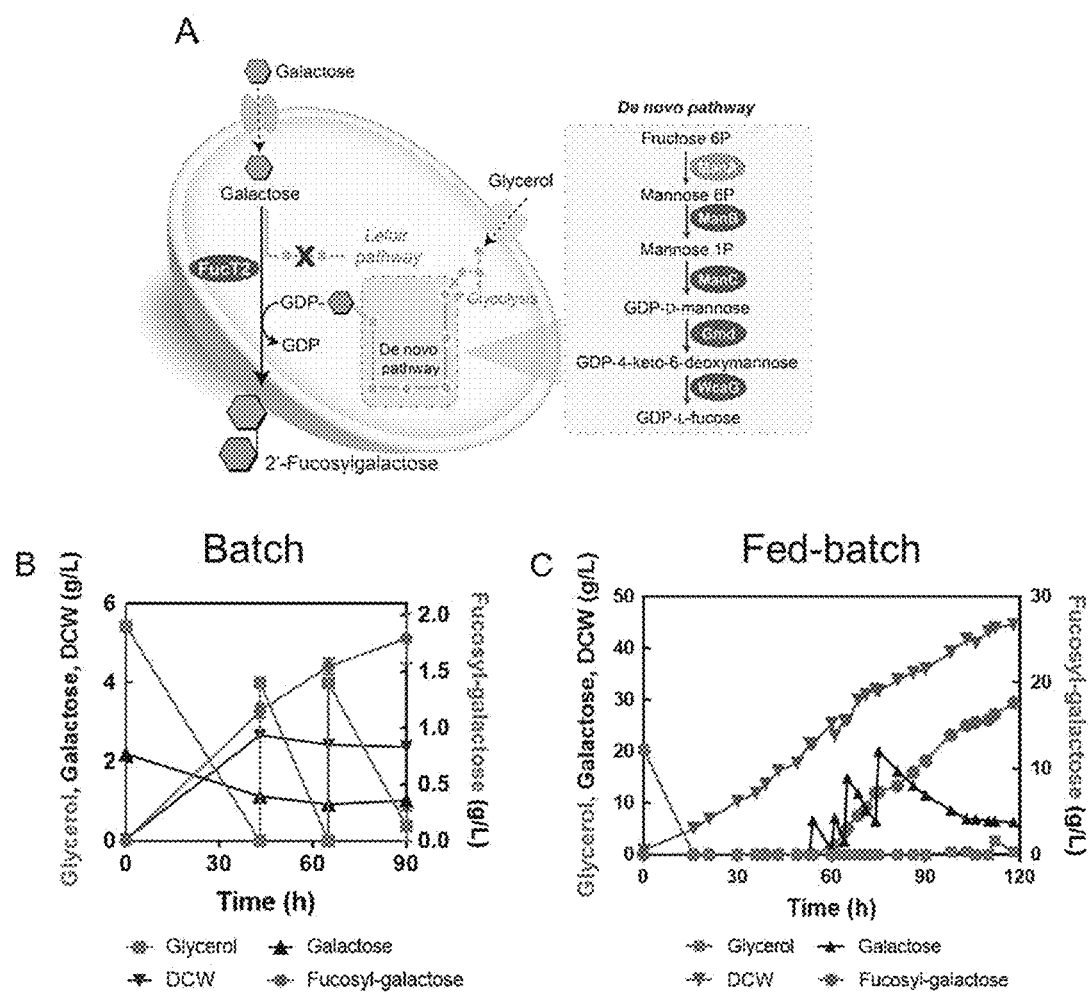
FIG. 6 illustrates a view for producing 2-fucosylgalactose using recombinant *E. coli* (A), and batch fermentation results (B) and fed-batch fermentation results (C) of recombinant *E. coli*.

<Example 3> Production of Fucosylgalactose Using Metabolic Engineering Technique To produce FGal, which is a bioactive substance from recombinant E. coli, metabolic engineering was employed and then fermentation was performed. A of FIG. 6 is a view for producing FGal using recombinant E. coli, in which to produce a GDP-fucose donor in E. coli cells, ManB, ManC, Gmd, and WcaG, which are enzymes involved in the de novo pathway, were introduced and galactose was supplied as an acceptor. To use galactose as an acceptor, an E. coli BL21 (DE3) strain, which is unable to metabolize galactose, was used as a host. Helicobacter pylori-derived FucT2 was used as α-1,2-fucosyltransferase, and glycerol was supplied as a carbon source. The recombinant E. coli was cultured in a LB broth medium containing 2 g/L of galactose and 5 g/L of glycerol at 37° C. for 6 hours, and IPTG was added thereto, followed by culture after the temperature was lowered to 25° C.

As illustrated in B of FIG. 6, 1.7 g/L of FGal was produced after batch fermentation for 90 hours.

C of FIG. 6 illustrates fed-batch fermentation results, in which about 12 g/L of FGal was produced after 90 hours of fermentation, and a maximum of 17.7 g/L of FGal was produced after 120 hours of fermentation.

<Example 4> Verification of Structure of 2-Fucosylgalactose Produced Through Metabolic Engineering Technique To confirm the structure of FGal produced via recombinant E. coli, FGal was purified from the culture. At this time, G-10 column resin and water were used as mobile phases to perform size-exclusion chromatography, and HPLC analysis was performed to confirm FGal fractions purified with high purity. In the HPLC analysis, a Rezex ROA-Organic Acid H+(8%) column (Phenomenex Inc) was used, and a 0.005N sulfuric acid solution was flowed at a rate of 0.6 mL/min at 50° C.

To confirm the α-1,2-glycosidic bond of the purified FGal, FGal as a substrate was subjected to the enzymatic reaction of α-1,2-fucosidase derived from Xanthomonas manihotis.

To this end, a gene encoding the α-1,2-fucosidase (NCBI Reference Sequence: WP_017167782.1) derived from Xanthomonas manihotis was introduced into a pETduet vector, and then the vector was transformed into the E. coli BL21 (DE3) strain. During the enzymatic reaction, 1 mg/mL of FGal was used as a substrate and 1 mg/mL of an intracellular crude enzyme of recombinant E. coli was used and the enzymatic reaction was performed in a 20 mM Tris-HCl buffer (pH 7.0) at 30° C. for 6 hours. At this time, as a control, an intracellular crude enzyme of recombinant E. coli containing an empty vector free of a gene encoding the enzyme was used to perform an enzymatic reaction.

Figure 7:
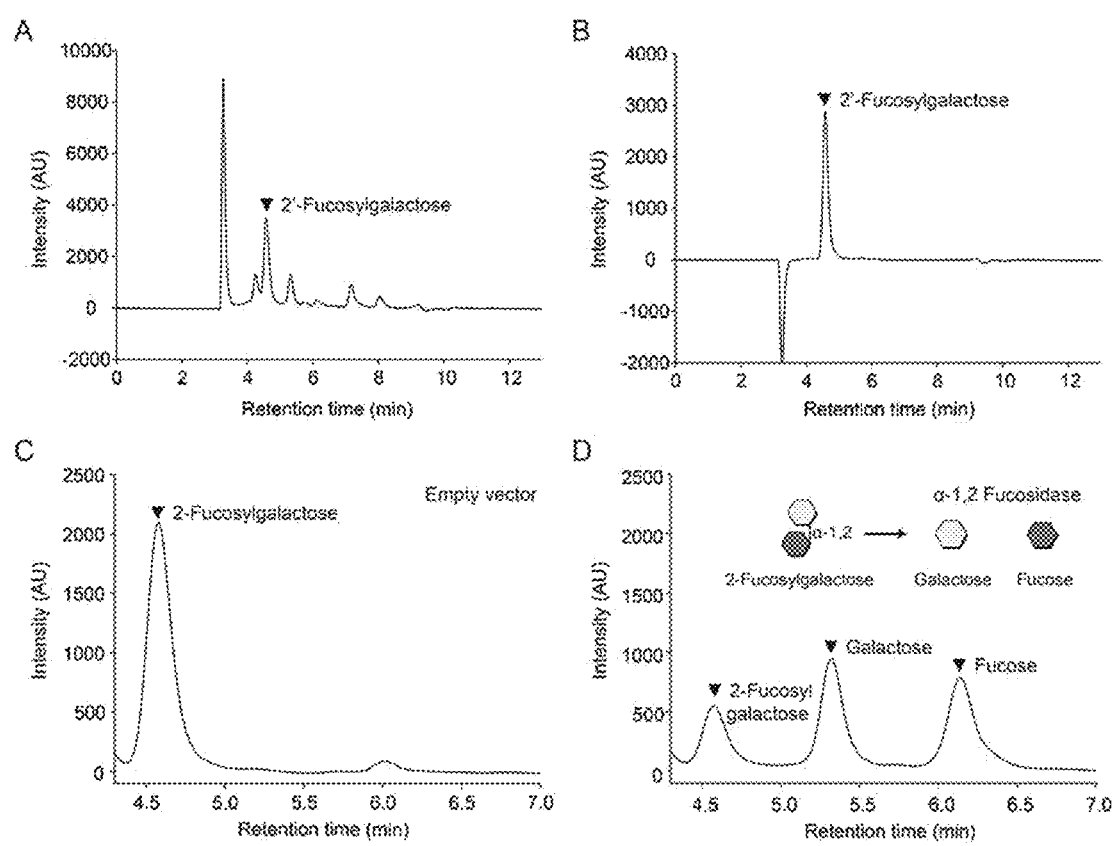
FIG. 7 illustrates 2-fucosylgalactose (B) separated and purified by size-exclusion chromatography using a G-10 column in a fermentation broth of recombinant *E. coli* (A), results of the enzymatic reaction of α-1,2-fucosyltransferase using 2-fucosylgalactose as a substrate to confirm the α-1,2-glycosidic bond of 2-fucosylgalactose (D), and results of the enzymatic reaction of α-1,2-fucosidase of a crude enzyme solution of recombinant *E. coli* including, as a control, an empty vector free of a gene encoding the enzyme (C).

As illustrated in FIG. 7, the α-1,2-glycosidic bond was verified through the enzymatic reaction of α-1,2-fucosidase of purified 2FG.

<Example 5> Verification of Prebiotic Properties of 2-Fucosylgalactose

To verify the prebiotic effect of FGal, the cell growth of strains such as *Bifidobacterium longum* subsp. *infantis* ATCC 15697 and *Bifidobacterium bifidum* DSM 20082 was monitored. In addition, to conduct a test for the capabilities of pathogenic microorganisms to ferment FGal, the cell growth of strains such as *E. coli* O1:K1:H7 and *Salmonella enterica* serovar *typhimurium* was monitored. At this time, the medium contained 10 g/L of BactoPeptone, 5 g/L of yeast extract, 2 g/L of $K_2HPO_4$ (anhydrous), 5 g/L of Na acetate (anhydrous), 2 g/L of $NH_4$ citrate tribasic, 0.2 g/L of Mg sulfate heptahydrate, 0.05 g/L of Mn sulfate, 1 mL/L of Tween 80 (polysorbate 80), 0.5 g/L of cysteine, and 3 g/L of purified FGal, and the strains were cultured at 37° C.

Figure 8:
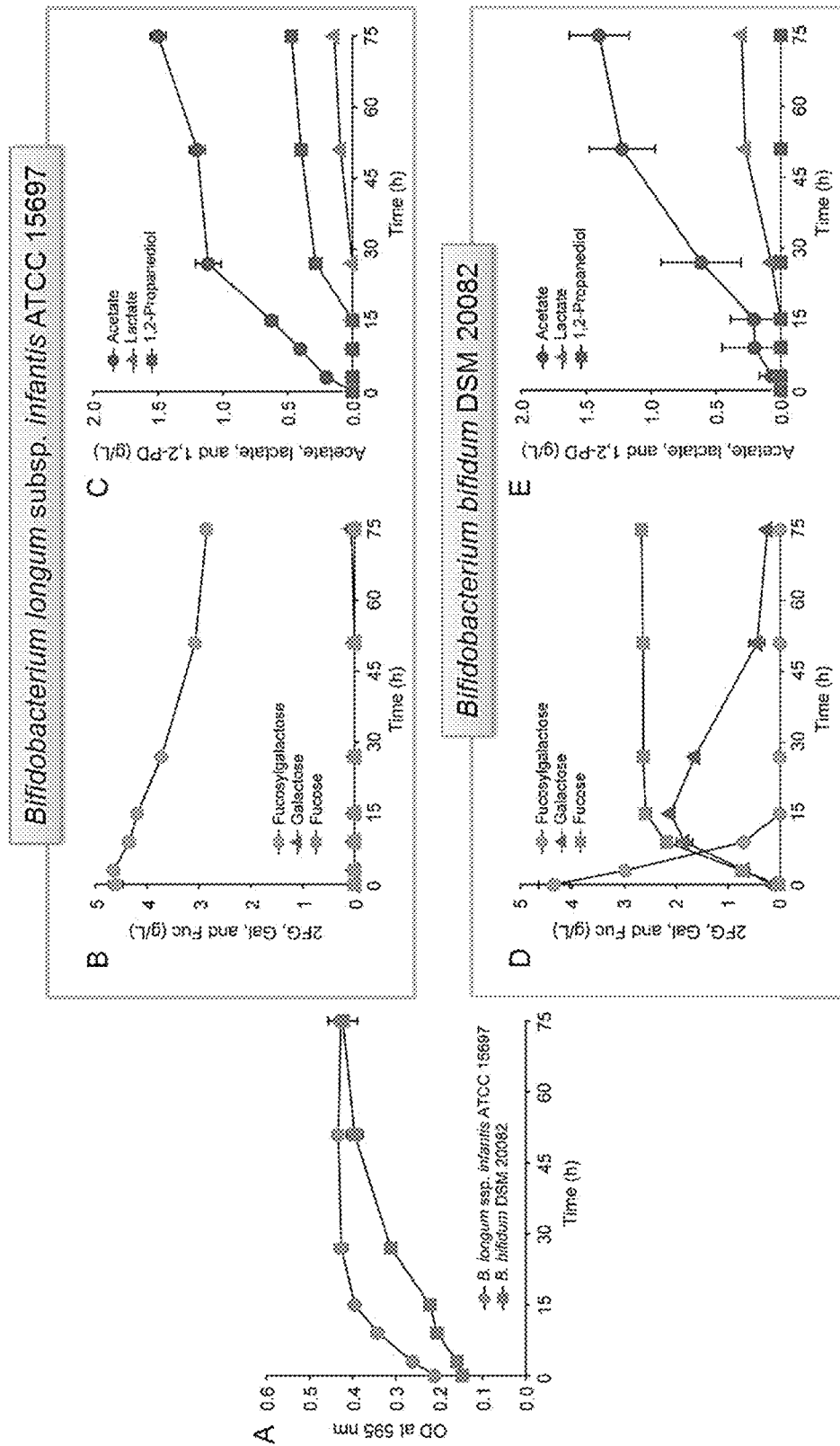
FIG. 8 illustrates the results of confirming the prebiotic activity of 2-fucosylgalactose in a strain belonging to the genus *Bifidobacterium*.

As illustrated in FIG. 8, it was confirmed that *Bifidobacterium bifidum* DSM 20082 first decomposed FGal into fucose and galactose extracellularly, and then metabolized a small amount of galactose, and *Bifidobacterium longum* subsp. *infantis* ATCC 15697 decomposed FGal into galactose and fucose through intracellular fucosidase and used both.

Figure 9:
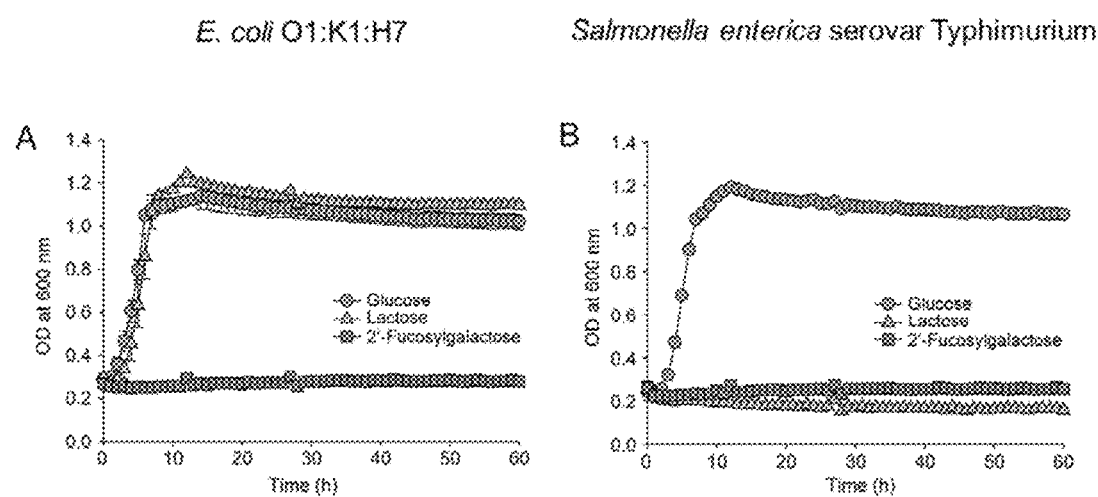
FIG. 9 illustrates the results of confirming the metabolism of 2-fucosylgalactose in pathogenic microorganisms.

As illustrated in FIG. 9, pathogenic microorganisms were unable to metabolize FGal.

According to the present invention, fucosyl-oligosaccharides can be used as prebiotic materials in medical, cosmetic, and food fields based on the prebiotic properties thereof.

What is claimed is:

1. A method of producing a fucosyl-oligosaccharide comprising reacting a sugar acceptor and a guanosine 5'-diphospho-p-L-fucose (GDP-L-fucose) donor with α-1,2-fucosyltransferase to produce a fucosyl-oligosaccharide, wherein the sugar acceptor is selected from the group consisting of glucose, galactose, cellobiose, lactose, fructose, sucrose, maltose, mannose, xylose, and agarobiose, the α-1,2-fucosyltransferase is selected from a sequence comprising the amino acid sequence of SEQ ID NO: 2, and the fucosyl-oligosaccharide is selected from the group consisting of 2'-fucosylglucose, 2'-fucosylgalactose, 2'-fucosylcellobiose, 2'-fucosylfructose, 2'-fucosylsucrose, 2'-fucosylmaltose, 2'-fucosylmannose, 2'-fucosylxylose, and 2'-fucosylagarobiose, wherein the reacting is performed in the presence of a vector for expressing a phosphomannomutase (ManB), a mannose 1-phosphate guanylytransferase (ManC), a GDP-D-mannose-4,6-dehydratse (Gmd) and a GDP-4-keto-6-deoxymannose 3,5-epimerase 4-reductase (WcaG) for producing the GDP-L-fucose.

2. The method of claim 1, wherein the reacting is performed at 20° C. to 40° C. for 3 hours to 24 hours.

3. A method of producing a fucosyl-oligosaccharide comprising culturing, in the presence of a sugar acceptor and glycerol, recombinant E. coli or yeast into which a vector for expressing ManB, ManC, Gmd, and WcaG involved in the de novo pathway for producing a guanosine 5'-diphospho-β-L-fucose (GDP-L-fucose) donor, and a vector for expressing α-1,2-fucosyltransferase are introduced, and separating and purifying the fucosyl-oligosaccharide from the *E. coli* or yeast culture, wherein the sugar acceptor is selected from the group consisting of glucose, galactose, cellobiose, lactose, fructose, sucrose, maltose, mannose, xylose, and agarobiose, and the α-1,2-fucosyltransferase is selected from a sequence comprising the amino acid sequence of SEQ ID NO: 2.

4. The method of claim 3, wherein the culturing is fed-batch culture.

5. The method of claim 4, wherein the fed-batch culture is performed at 25° C. to 37° C. for 2 hours to 60 hours, and isopropyl β-D-1-thiogalactopyranoside (IPTG) is added thereto, followed by further fed-batch culture at 20° C. to 30° C. for 60 hours to 150 hours.

\* \* \* \* \*